(12) United States Patent
Reydel

(10) Patent No.: US 9,549,734 B2
(45) Date of Patent: Jan. 24, 2017

(54) ENDOSCOPIC STAPLING DEVICE, RELATED STAPLES, AND METHODS FOR USE

(75) Inventor: Boris Reydel, West Caldwell, NJ (US)

(73) Assignee: BOSTON SCIENTIFIC SCIMED, INC., Maple Grove, MN (US)

(*) Notice: Subject to any disclaimer, the term of this patent is extended or adjusted under 35 U.S.C. 154(b) by 448 days.

(21) Appl. No.: 12/386,095

(22) Filed: Apr. 14, 2009

(65) Prior Publication Data

US 2009/0259250 A1 Oct. 15, 2009

Related U.S. Application Data

(60) Provisional application No. 61/124,000, filed on Apr. 14, 2008.

(51) Int. Cl.
| | |
|---|---|
| A61B 17/064 | (2006.01) |
| A61B 17/068 | (2006.01) |
| A61B 17/00 | (2006.01) |

(52) U.S. Cl.
CPC ....... *A61B 17/0682* (2013.01); *A61B 17/0057* (2013.01); *A61B 2017/00668* (2013.01); *A61B 2017/0645* (2013.01)

(58) Field of Classification Search
CPC ............................ A61B 17/064; A61B 17/068

USPC .............. 606/139, 142, 143, 151, 157, 158, 606/213–217, 219, 221
See application file for complete search history.

(56) References Cited

U.S. PATENT DOCUMENTS

| | | | | |
|---|---|---|---|---|
| 3,939,828 | A * | 2/1976 | Mohr et al. ................... | 606/916 |
| 4,887,601 | A * | 12/1989 | Richards ....................... | 606/219 |
| 4,961,743 | A * | 10/1990 | Kees et al. .................... | 606/158 |
| 5,222,961 | A | 6/1993 | Nakao et al. | |
| 5,413,584 | A * | 5/1995 | Schulze ........................ | 606/219 |
| 5,478,353 | A * | 12/1995 | Yoon ............................ | 606/213 |
| 5,984,949 | A * | 11/1999 | Levin ........................... | 606/216 |
| 6,273,903 | B1 * | 8/2001 | Wilk ............................. | 606/219 |
| 7,303,526 | B2 * | 12/2007 | Sharkey et al. ................ | 600/37 |
| 7,485,124 | B2 * | 2/2009 | Kuhns et al. .................. | 606/151 |
| 7,556,647 | B2 * | 7/2009 | Drews et al. ................. | 623/2.11 |
| 7,879,052 | B2 * | 2/2011 | Adams et al. ................ | 606/157 |
| 2002/0068947 | A1 * | 6/2002 | Kuhns et al. ................. | 606/143 |
| 2003/0050682 | A1 * | 3/2003 | Sharkey et al. .............. | 607/126 |
| 2006/0155310 | A1 * | 7/2006 | Binmoeller .................... | 606/151 |

* cited by examiner

*Primary Examiner* — Kathleen Holwerda
(74) *Attorney, Agent, or Firm* — Fay Kaplun & Marcin, LLP

(57) ABSTRACT

A material-fastening device and related fastener and methods for use, and more particularly, a device with segments of the fastener capable of being independently attached to different sides of a gap in the material.

20 Claims, 10 Drawing Sheets

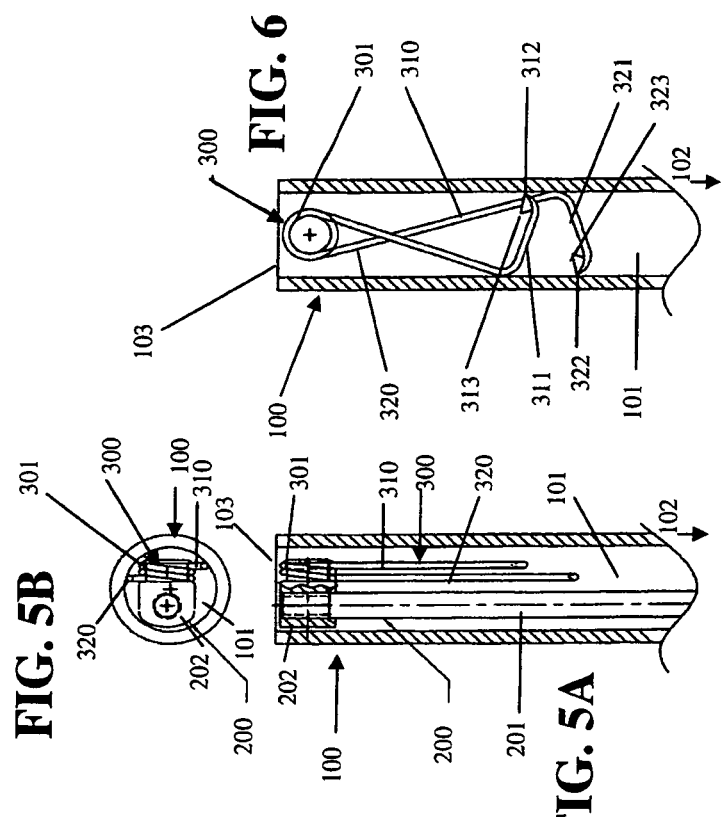

ENDOSCOPIC STAPLING DEVICE, RELATED STAPLES, AND METHODS FOR USE

This application claims the benefit of U.S. Provisional Application No. 61/124,000, filed Apr. 14, 2008, the contents of which are hereby incorporated by reference.

BACKGROUND OF THE INVENTION (1) Field of the Invention

This invention relates to an endoscopic tissue-fastening device and related fastener and methods for use, and more particularly, a device which allows segments of the fastener to be independently attached to the tissue (2) Description of Related Art Endoscopic stapling devices have been created in which a staple or other fastening device stored in a tubular member is pushed from the remote end of the tubular member to seal a gap or hole in flesh. U.S. Pat. No. 7,175,648 to Nakao, U.S. Pat. No. 5,222,961 to Nakao et al., U.S. Pat. No. 7,063,715 to Onuki et al., U.S. Pat. No. 6,872,214 to Sonnenschein et al., U.S. Pat. No. 5,782,397 to Koukline, and U.S. Pat. No. 6,626,916 to Yeung et al.

However, these devices initially puncture or grasp the tissue to be fastened in the same "forward" direction as the extension of the tubular member or other extension device, that is, in the direction from the proximate end of the tubular member which allows for the devices to be held to the remote end of the tubular member where the staples or other fasteners are dispensed. Thus, the tissue acted upon is the tissue directly in front of the remote end of the tubular member. When the tubular member in these devices extend towards the exterior of the stomach or other lumen-containing organ from the interior of the stomach or the other lumen-containing organ, these portions of the staple, or a grasping device, grasp or puncture the interior, mucosal/submucosal layer of the stomach or the interior layer of the other lumen-containing organ.

This disclosure identifies special problems that are presented by the use of these devices on the wall of the stomach. For example, there is a risk of grasping or puncturing organs on the exterior of the intended organ. The interior mucosal/submucosal layer of the stomach is, by comparison to the exterior muscularis/serosal layer of the stomach, a very thick, loose, and slippery layer. The mucosal layer is difficult to grasp directly, and an attempt to puncture it from the interior of the stomach creates the risk of puncturing organs on the other side. These issues can extend surgery time and create a health risk to the patient. However, the exterior muscularis/serosal layer is much easier to grasp and puncturing it from the exterior of the stomach is much safer.

Moreover, these devices simultaneously expose, and simultaneously fasten tissue with, two opposite segments of the fastener. This does not allow for separate exposure and fastening with each of the two opposite segments. As a result, no fastening may occur until after the tissue on each side of the wound is moved near the tissue on the other side of the wound, and a sole tissue-embedded segment may not be used to reposition the tissue in preparation for embedding of the other segment.

Therefore, a need exists for a new and improved stapling device and related staple, for endoscopic stomach wall stapling or other hollow organ wall stapling or other uses, that provides for initial grasping or puncturing to occur on the exterior layer, in a backwards direction, and a need also exists for a new and improved stapling device that allows for independent exposure and embedding of each of two segments of the fastener.

SUMMARY OF THE INVENTION

The present invention relates to a material-joining device, and in particular to a material-joining device having: (1) a fastener having a first segment with a first material-securing mechanism/means, a second segment with a second material-securing mechanism/means, and a connection portion connecting the first segment to the second segment, wherein the first material-securing mechanism is configured to secure material independently of the second material-securing mechanism; and (2) a holding mechanism/means for releasably holding the fastener.

In another embodiment of the invention, the invention additional has an exposing mechanism/means for exposing the first material-securing mechanism independently of exposing the second material-securing mechanism, and for exposing the second material-securing mechanism.

In yet another embodiment of the invention, the first material-securing mechanism is a first hook, and the second material-securing mechanism is a second hook. In one embodiment, the first hook and the second hook each have at least one sharp puncturing portion and at least two barbed portions.

In a further embodiment of the invention, at least one of the first material-securing mechanism and the second material-securing mechanism has at least two subsections, each of which subsections has a sub-mechanism/sub-means for securing material. In one embodiment, the sub-mechanism has a sharp puncturing portion and a barbed portion.

In another embodiment, the device further has at least one additional fastener, wherein the holding mechanism is also for holding the at least one additional fastener simultaneously with holding the fastener.

In yet another embodiment, the holding mechanism extends primarily in one direction from the fastener, and the first material-securing mechanism and the second-material securing mechanism are positioned such that, when securing material, they each extend in approximately this one direction.

In a further embodiment, the first material-securing mechanism and the second-material securing mechanism are positioned such that, when securing material, they extend in approximately opposite directions from each other.

In another embodiment, the connection portion has at least one hinge.

In yet another embodiment, the exposing mechanism includes a part of the fastener for storing potential energy and applying it to the first segment and applying it to the second segment, a resisting mechanism/means for selectively resisting movement of the first segment which would otherwise be caused by the application of the potential energy to the first segment and for selectively resisting movement of the second segment which would otherwise be caused by the application of the potential energy to the second segment independently of resisting movement of the first segment which would otherwise be caused by the application of the potential energy to the first segment.

In a further embodiment, the part of the fastener for storing potential energy and applying it to the first segment and applying it to the second segment is a coil.

In another embodiment, the second segment has a longer length than the first segment, the resisting mechanism is a tubular member, having a proximate end and a remote end, for resisting movement of the first segment which would otherwise be caused by the application of the potential energy to the first segment until the tubular member is moved, in the direction from the remote end to the proximate end, a first distance relative to the holding mechanism, and for resisting movement of the second segment which would otherwise be caused by the application of the potential energy to the second segment until the tubular member is moved, in the direction from the remote end to the proximate end, a second distance relative to the holding mechanism, which second distance is greater than the first distance.

In a separate embodiment, the invention relates to a stapler having (1) a tubular member having and extending between a proximate end and a remote end; (2) a rod at least partially disposed within the tubular member, extending in the same direction as the tubular member, and movable in the direction of extension of the tubular member relative to the tubular member; and (3) a staple having a first segment of a first length, a first hook which is a part of the first segment, a second segment of a second length greater than the first length, a second hook which is part of the second segment, and a connection portion connecting the first segment to the second segment, wherein the staple is configured such that the staple may be removably attached to the rod and may be folded such that at least the first hook and the second hook are disposable within the tubular member with the first segment and the second segment extending from the connection portion such that the distances from the first segment and the second segment to the proximate end are each less than the distance from the connection portion to the proximate end.

In another embodiment of the invention, the staple is further configured such that potential energy is stored in the staple when it is folded.

In yet another embodiment, the staple is further configured such that the potential energy causes the first segment to extend approximately perpendicularly to the direction of extension of the tubular member when the staple is moved by the rod relative to the tubular member such that the first segment is positioned entirely beyond the remote end of the tubular member.

In a further embodiment, the staple is further configured such that the second hook which is a part of the second segment remains disposed within the tubular member when the staple is moved by the rod relative to the tubular member such that the first segment is positioned entirely beyond the remote end of the tubular member.

In another embodiment, the staple is further configured such that the potential energy causes the second segment to extend approximately perpendicularly to the direction of extension of the tubular member and in approximately the opposite direction from the direction of extension of the first segment when the staple is moved by the rod relative to the tubular member a further distance such that the second segment is positioned entirely beyond the remote end of the tubular member.

In yet another embodiment, the staple is further configured such that when the potential energy causes the first segment to extend approximately perpendicularly to the direction of extension of the tubular member and the second segment to extend approximately perpendicularly to the direction of extension of the tubular member and in approximately the opposite direction from the direction of extension of the first segment, the first hook and the second hook are directed approximately in the direction from the remote end to the proximate end.

In another aspect of the present invention, there is a method for using a material-joining device having (1) a fastener having a first segment with a first material-securing mechanism, a second segment with a second material-securing mechanism, and a connection portion connecting the first segment to the second segment and (2) a holding mechanism for releasably holding the fastener, to join material separated by a gap, which method involves: (1) securing a portion of the material on one side of the gap with the first material-securing mechanism; (2) independently of securing the portion of the material on the one side of the gap with the first material-securing mechanism, securing a portion of the material on a second side of the gap with the second material-securing mechanism; and (3) detaching the fastener from the holding mechanism.

In another embodiment, the method further involves: after securing the portion of the material on the one side of the gap with the first material-securing mechanism, but before securing the portion of the material on the second side of the gap with the second material-securing mechanism, using the first material-securing mechanism to move the portion of the material on the one side of the gap closer to the portion of the material on the second side of the gap.

In yet another embodiment, the material-joining device used in the method further has an exposing mechanism, and the method further involves: (1) before securing the portion of the material on the one side of the gap with the first material-securing mechanism, exposing the first material-securing mechanism with the exposing mechanism; and (2) before securing the portion of the material on the second side of the gap with the second-material securing mechanism, exposing the second material-securing mechanism with the exposing mechanism independently of exposing the first material-securing mechanism with the exposing mechanism.

In a further embodiment, the material involved in the method is a wall of a lumen-containing organ having an exterior layer and an interior layer, and the gap is a wound in the wall of the lumen-containing organ.

In another embodiment, the portion of the wall on the one side of the wound is secured by contact with the first material-securing mechanism which initially occurs on a side-edge of the wall, and wherein the portion of the wall on the second side of the wound is secured by contact with the second material-securing mechanism which initially occurs on a side-edge of the wall.

In yet another embodiment, the portion of the wall on the one side of the wound is secured by contact with the first material-securing mechanism which initially occurs on an exterior layer of the wall, and wherein the portion of the wall on the second side of the wound is secured by contact with the second material-securing mechanism which initially occurs on the exterior layer of the wall.

In another embodiment, the method further involves: allowing pressure within the lumen-containing organ to cause the interior layer of the portion of the wall on the one side of the wound and the interior layer of the portion of the wall on the second side of the wound to swing towards each other, using at least one of the first material-securing mechanism and the second material-securing mechanism as at least a portion of a hinge about which the swinging takes place.

In a separate aspect of the invention, there is a method for using a stapler having (1) a tubular member having and extending between a proximate end and a remote end, (2) a rod at least partially disposed within the tubular member, and (3) a staple having a first segment of a first length, a first hook which is a part of the first segment, a second segment of a second length greater than the first length, a second hook which is a part of the second segment, and a connection portion connecting the first segment to the second segment, wherein the staple is removably attached to the rod and is folded such that at least the first hook and the second hook are disposed within the tubular member, to seal a wound in the wall of a patient's lumen-containing organ, which method involves: (1) inserting the remote end of the tubular member into the lumen through an opening connecting the exterior of the patient to the lumen; (2) inserting the remote end of the tubular member through the wound in the lumen-containing organ to the exterior of the lumen-containing organ; (3) moving the rod relative to the tubular member, in the direction from the proximate end to the remote end, such that the first segment of the staple extends beyond the remote end of the tubular member, such that potential energy stored in the staple causes the first segment to extend approximately perpendicularly to the direction of extension of the tubular member; (4) moving the rod such that the first hook is in contact with a portion of the exterior layer which is on one side of the wound; (5) pulling the rod, in the direction from the remote end to the proximate end, such that at least a portion of the first hook is pulled into the portion of the exterior layer on the one side of the wound; (6) moving the rod relative to the tubular member, in the direction from the proximate end to the remote end, such that the second segment of the staple extends beyond the remote end of the tubular member, such that potential energy stored in the staple causes the second segment to extend approximately perpendicularly to the direction of extension of the tubular member and approximately parallel to the exterior layer; (7) moving the rod, such that the portion of the exterior layer which is on the one side of the wound is moved by the first hook closer to a portion of the exterior layer which is on a second side of the wound, and such that the second hook is in contact with a portion of the exterior layer which is on the second side of the wound; (8) pulling the rod, in the direction from the remote end to the proximate end, such that at least a portion of the second hook is pulled into the portion of the exterior layer which is on the second side of the wound; (9) detaching the staple from the rod; and (10) removing the rod and tubular member from the patient through the opening.

In another embodiment, the lumen-containing organ involved in the method is the stomach.

In a separate aspect of the invention, there is a method for using a fastening device having (1) an extension portion having a proximate end and a remote end, (2) a fastener-holding portion secured by the extension portion, (3) a fastener removably held by the fastener-holding portion having a first segment of a first length, a first material-securing portion which is a part of the first segment, a second segment of a second length longer than the first length, a second material-securing portion which is a part of the second segment, and a connection portion connecting the first segment to the second segment, wherein at least a portion of the first segment and a portion of the second segment are secured within the extension portion, to fasten together material separated by a gap, which method involves: (1) inserting the remote end of the extension portion through the gap; (2) moving the fastener-holding portion relative to the extension portion such that the first segment of the fastener extends beyond the remote end of the extension portion; (3) moving the first segment such it extends approximately perpendicularly to the direction of extension of the extension portion; (4) moving the fastener-holding portion such that the first material-securing portion is in contact with a portion of the material on one side of the gap that is most distant from the proximate end in the direction from the proximate end to the remote end; (5) securing the portion of the material on one side of the gap with the first material-securing portion; (6) moving the fastener-holding portion relative to the extension portion such that the second segment of the fastener extends beyond the remote end of the extension portion; (7) moving the second segment such it extends approximately perpendicularly to the direction of extension of the extension portion; (8) moving the fastener-holding portion such that the second material-securing portion is in contact with a portion of the material on a second side of the gap that is most distant from the proximate end in the direction from the proximate end to the remote end; (9) securing the portion of the material on the second side of the gap with the second material-securing portion; and (10) detaching the fastener from the fastener-holding portion.

In another embodiment, in the method the extension portion is a tubular member, the fastener-holding portion is a rod, the fastener is a staple, the first and second material-securing portions are hooks, the gap is a wound in a lumen-containing organ, and the material is a wall of the lumen-containing organ.

In yet another embodiment, the method is performed endoscopically.

In a further embodiment, in the method moving the first and second segments of the staple such that they extend approximately perpendicularly to the direction of extension of the tubular member is performed by energy stored within the staple.

In another embodiment, in the method the securing of the portion of the wall of the lumen-containing organ on one side of the wound with the first hook and the securing of the portion of the wall of the lumen-containing organ on a second side of the wound with the second hook are accomplished by pulling the hooks into the portions through a movement of the rod in the direction from the remote end to the proximate end;

In a separate aspect of the present invention, there is a method for using a material-joining device having (1) a fastener having a first segment with a first material-securing mechanism, a second segment with a second material-securing mechanism, and a connection portion connecting the first segment to the second segment and (2) a holding mechanism for releasably holding the fastener, to reduce bleeding of a blood vessel having tissue on one side and tissue on a second side, which method involves: (1) securing the tissue on the one side of the blood vessel with the first material-securing mechanism; (2) moving the tissue on the one side of the blood vessel by moving the first material-securing mechanism; (3) independently of securing the tissue on the one side of the blood vessel with the first material-securing mechanism, securing the tissue on the second side of the blood vessel with the second material-securing mechanism; (4) allowing the tissue on the one side of the blood vessel to return towards its original position, such as to pinch the blood vessel between the tissue on the one side of the blood vessel and the tissue on the second side of the blood vessel; and (5) detaching the fastener from the holding mechanism.

In another embodiment, in the method at least one of the securing of the tissue on the one side of the blood vessel and the securing of the tissue on the second side of the blood vessel involves compressing tissue on at least one side of the blood vessel, and allowing the tissue on the one side of the blood vessel to return towards its original position involves allowing the compressed tissue to decompress.

In a separate aspect of the present invention, there is a method for using a material-joining device having (1) a fastener having a first segment with a first material-securing mechanism, a second segment with a second material-securing mechanism, and a connection portion connecting the first segment to the second segment and (2) a holding mechanism for releasably holding the fastener, to reduce the size of an ulcer-like lesion having tissue on one side and tissue on a second side, which method involves: (1) securing the tissue on the one side of the ulcer-like lesion with the first material-securing mechanism, such that the tissue on the one side of the ulcer-like lesion is compressed; (2) moving the tissue on the one side of the ulcer-like lesion by moving the first material-securing mechanism; (3) independently of securing the tissue on the one side of the ulcer-like lesion with the first material-securing mechanism, securing the tissue on the second side of the ulcer-like lesion with the second material-securing mechanism, such that the tissue on the second side of the ulcer-like lesion is compressed; (4) allowing the tissue on the one side of the ulcer-like lesion and the tissue on the second side of the ulcer-like lesion to decompress, such as to reduce the size of the ulcer-like lesion; and (5) detaching the fastener from the holding mechanism.

In another embodiment, the in the method at least one of the securing of the tissue on the one side of the ulcer-like lesion and the securing of the tissue on the second side of the ulcer-like lesion involves initially contacting the tissue at a side-edge of the ulcer-like lesion.

In a separate embodiment of the present invention, the invention relates to a fastener having: (1) a first segment having a first material-securing mechanism; (2) a second segment having a second material-securing mechanism, wherein the first material-securing mechanism is configured to secure material independently of the second material-securing mechanism; and (3) a connection portion connecting the first segment to the second segment.

In another embodiment, the fastener is a staple.

In yet another embodiment the first material-securing mechanism is a first hook, and the second material-securing mechanism is a second hook.

In a further embodiment, at least one of the first hook and the second hook has at least one sharp puncturing portion and at least two barbed portions.

In another embodiment, at least one of the first material-securing mechanism and the second material-securing mechanism has at least two subsections, each of which subsections has a sub-mechanism configured to secure material.

In yet another embodiment, the sub-mechanism has a sharp puncturing portion and a barbed portion.

In a further embodiment, the connection portion has at least one hinge.

In another embodiment, the fastener is configured to store potential energy and apply it to the first segment and apply it to the second segment.

In yet another embodiment, the potential energy is stored in the connection portion.

In a further embodiment, the potential energy is stored in a coil.

In another embodiment, the second segment has a longer length than the first segment.

In yet another embodiment, the fastener is configured to store the potential energy when the fastener is folded.

In a further embodiment, the fastener is configured to use the potential energy to return to an unfolded state if the return is not resisted.

In another embodiment, the first material-securing mechanism and the second material-securing mechanism extend in approximately the same direction.

In yet another embodiment, the first material-securing mechanism and the second material-securing mechanism extend in approximately opposite directions.

BRIEF DESCRIPTION OF THE DRAWINGS

FIG. 4A is a front-view of an unfolded staple according to one embodiment of the present invention;

FIG. 4B is a top-view of an unfolded staple according to one embodiment of the present invention;

FIG. 5A is a side-view of the remote portion of the device according to one embodiment of the present invention;

FIG. 5B is a top-view of the remote portion of the device according to one embodiment of the present invention;

FIG. 6 is a front-view of a folded staple within a remote portion of a tube according to one embodiment of the present invention.

DETAILED DESCRIPTION OF THE INVENTION

Figure 1:
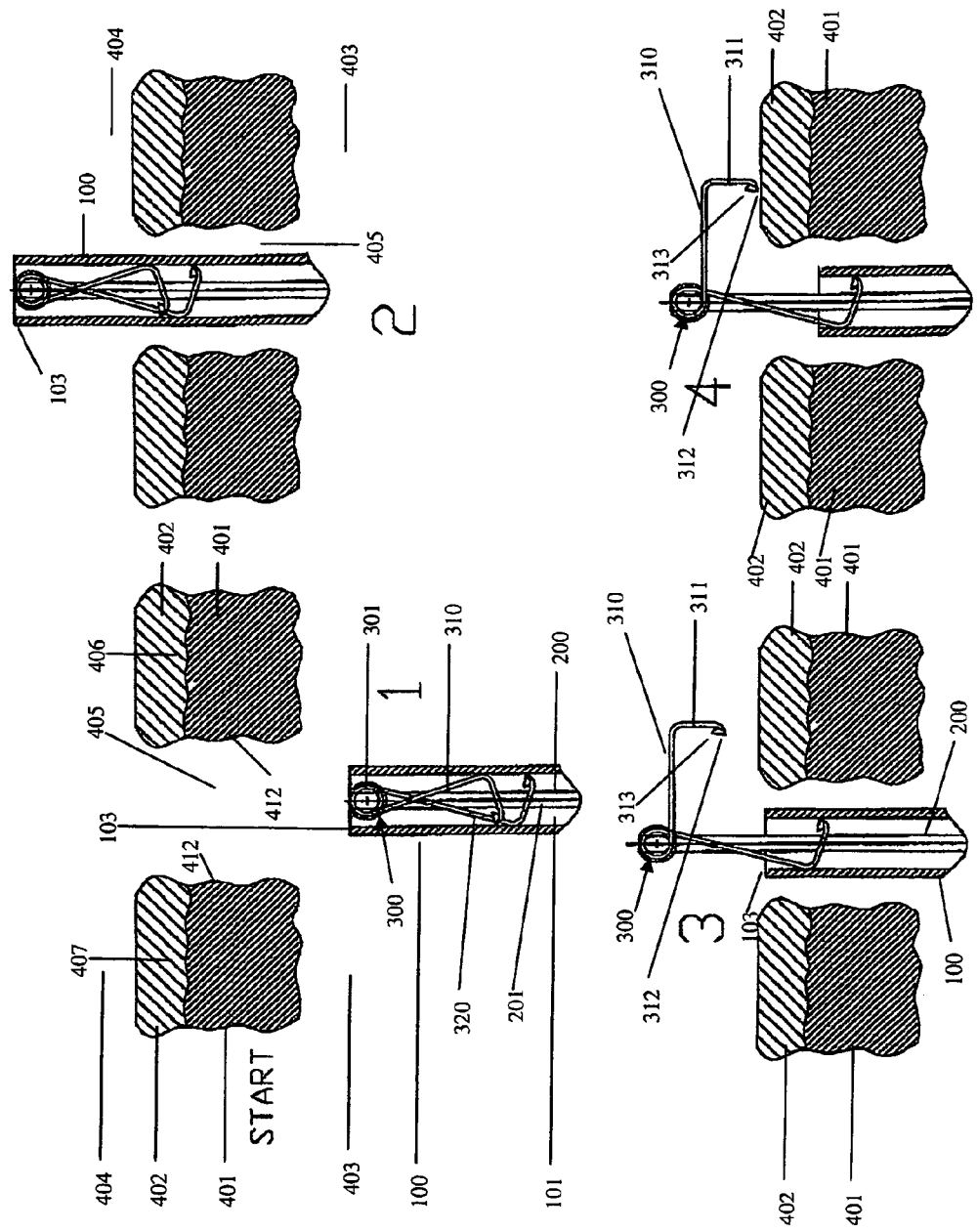
FIG. 1 shows initial steps 1-4 of a method of using one embodiment of the present invention.
Figure 2:
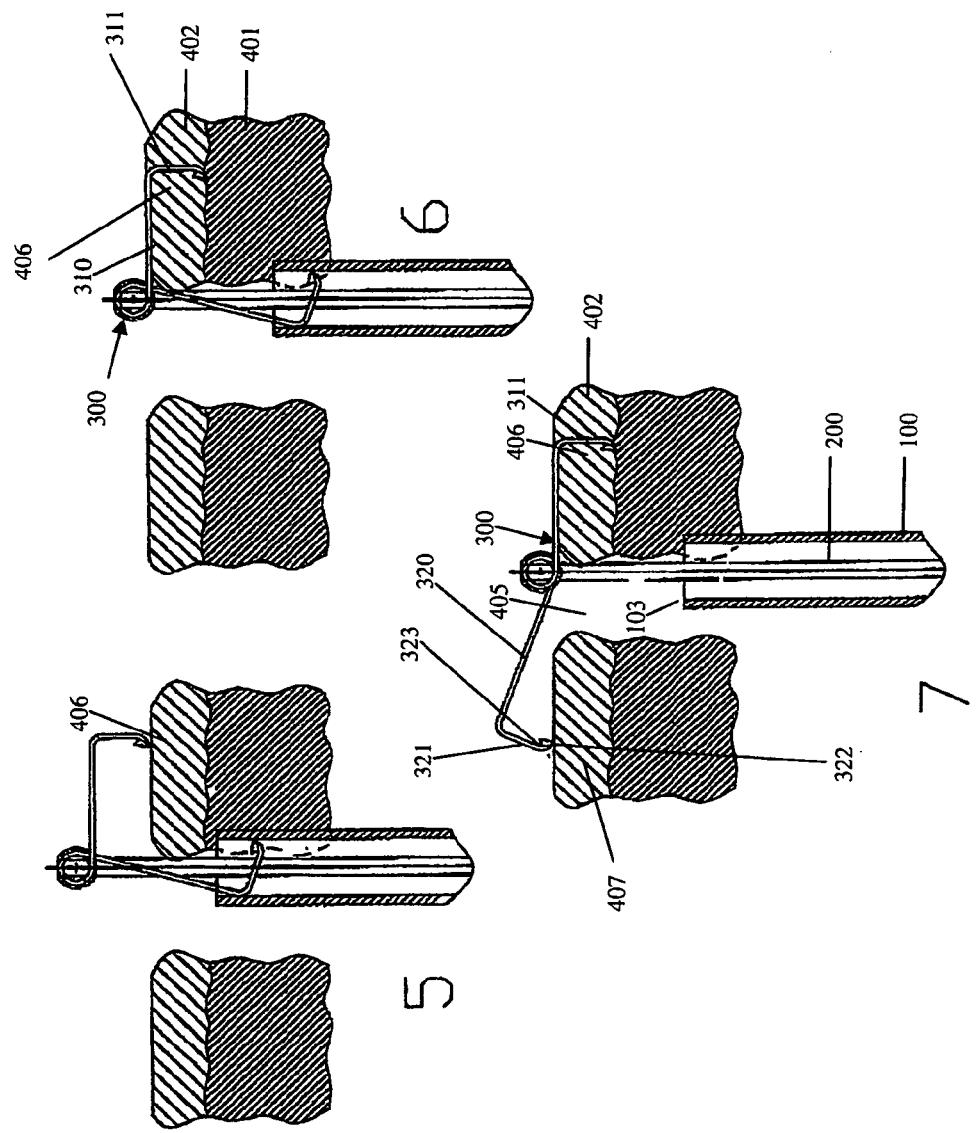
FIG. 2 shows steps 5-7 of a method of using one embodiment of the present invention.
Figure 3:
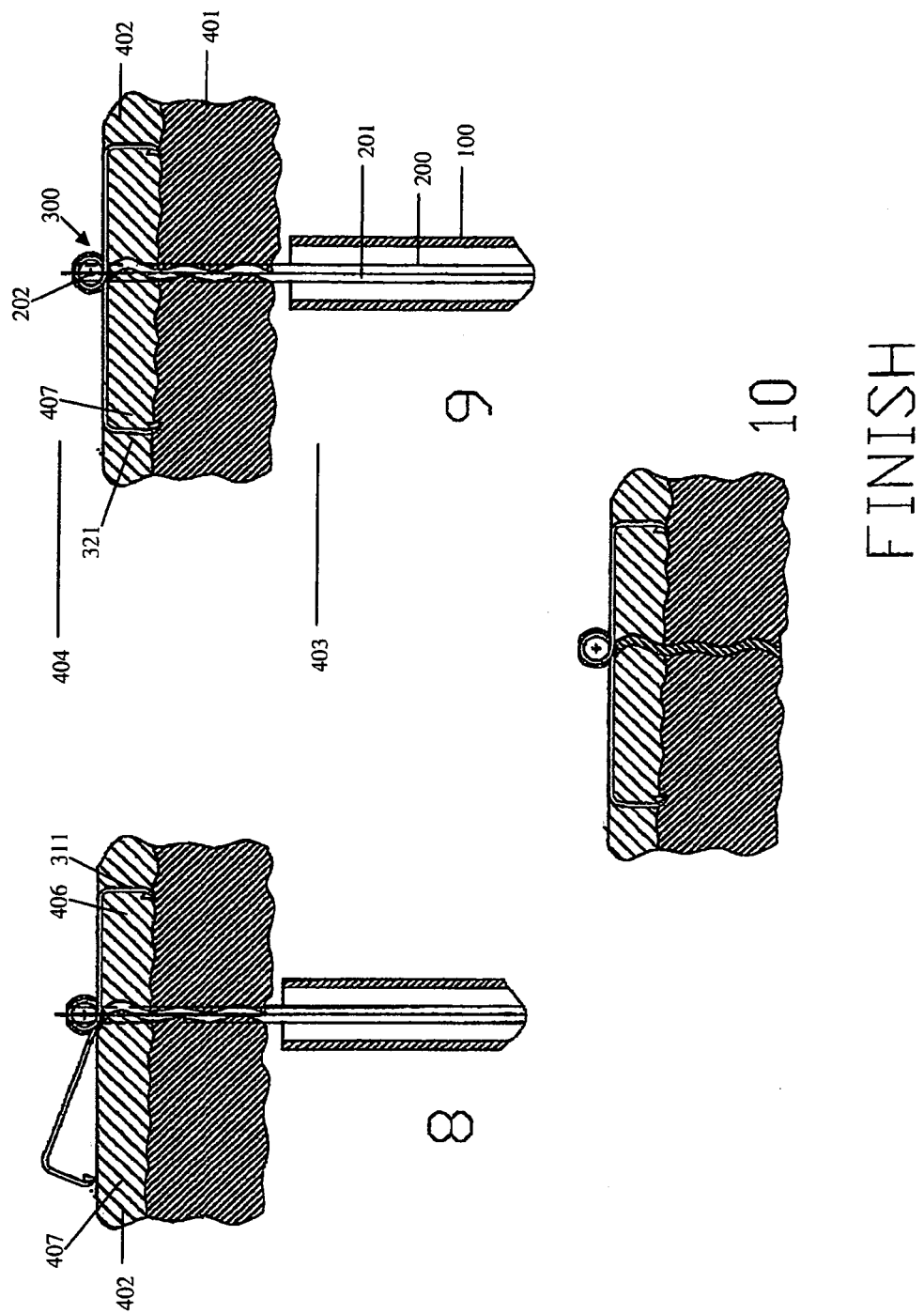
FIG. 3 shows final steps 8-10 of a method of using one embodiment of the present invention.

The present invention relates to a material-fastening device and related staple 300 or other fastener, and in particular to a device with segments 310; 320 of the fastener capable of being independently attached to different sides of a gap 405 in the material, as exemplified in FIGS. 1-3.

One embodiment of the present invention is shown in FIGS. 4A-6. As shown in FIGS. 5A-6, a tube 100 or other extension device is elongate, flexible, and tubular, and has an outer diameter small enough for extending longitudinally through a flexible tubular endoscope member, and a hollow interior 101. The tube may be made of any appropriate material, such as a plastic. The tube 100 has a proximate end 102 and a remote end 103, and extends between these ends. While the tube 100 is flexible, and thus in use may curve, the direction extending from the proximate end 102 to the remote end 103, which travels along the tube however it may be curved, shall be referred to as "forwards,", while the direction extending from the remote end 103 to the proximate end 102, shall be referred to as "backwards." The proximate end 102 is used for holding and controlling the device, or for attachment to a handle or other element which allows for holding and controlling the device. During a medical procedure using the device, the tube 100 is inserted remote end 103 first into the patient.

The rod 200, as shown in FIGS. 5A and 5B, which is disposed at least partially within the tube 100, is likewise elongate, flexible, and tubular, and is shaped such that it occupies a portion of the hollow interior 101 of the tube 100. It may also be made of a plastic. As the rod 200 occupies only a portion of the hollow interior 101, it may move relative to the tube 100 by being inserted further forward or pulled backward. This forward or backward movement may occur by the direct application of force to the rod 200. However, forward or backward movement may also occur by application of force to an attachment to the rod, such as a plunger.

The staple 300, as shown in FIG. 4A, has a first segment 310 and a second segment 320, a first hook 311 and a second hook 321 which are a part of the first segment 310 and the second segment 320, respectively, and a connection portion 301 connecting the first segment 310 and the second segment 320 to each other. The staple 300 may be made of any appropriate non-biodegradable material, such as metals, alloys, or plastics, or biodegradable material, such as polylactic resin, polycolic resin or other polymer. The first segment 310 is not as long as the second segment 320, making the staple 300 asymmetric. In FIG. 4B, the first segment 310 is shown as being 2.50 mm shorter than the second segment 320. However, other appropriate relative lengths may be used. The connection portion 301, according to this embodiment, is a coil and is removably attached to the rod 200. The coil is shown in FIG. 4A as being 2 mm in diameter, although other appropriate sizes may be used. When the coil is in a relaxed state, as shown in FIGS. 4A and 4B, at least a portion of each of the first segment 310 and the second segment 320 extend in approximately opposite directions from the coil, and, in this state, the first segment 310 and the second segment 320 extend approximately perpendicularly to the forward direction. However, as shown in FIG. 4A, the first hook 311 and the second hook 321 in this embodiment do not extend in the same direction as the segments 310; 320 of which they are a part, but instead are directed approximately backward. In other embodiments however, such as the embodiment shown in FIG. 7, the hooks 311; 321 do extend in the same directions as their respective segments 310; 320. In the embodiment shown in FIG. 4A, each of the hooks 311; 321 has a length-adding portion, shown in FIG. 4A as being approximately 3.00 mm in length, although other appropriate lengths may be used, which increases the amount of backward extension, a sharp portion 312; 322 for puncturing, and a barbed portion 313; 323 for preventing the hook 311; 321 from becoming dislodged once inserted into tissue such as a stomach wall, or another material. The hooks 311; 321 may be used both for holding the staple 300 in the material, and for moving the material by applying force with the rod 200 as shown in FIGS. 5A and 5B, which force travels through the rod 200, through an attachment mechanism 202 if one is used as in this embodiment, and through the staple 300 to the hooked material. By moving the material in this way, the edges 412 of the gap/wound 405, as shown in FIGS. 1-3, may be moved together which may facilitate quicker healing.

The connection portion 301 of the staple 300 in the one embodiment, as shown in FIG. 5A, is removably attached to the rod 200 by a threading mechanism 201 which runs through the rod 200, and by an attachment mechanism 202. This threading mechanism 201 and attachment mechanism 202 allow for the staple 300 to be securely held by the rod 200, but rotating the threading mechanism 201 causes the staple 300 to come loose from the rod 200, allowing for convenient removal. However, other appropriate means of attaching the staple 300 to the rod 200 may be used, for example, mechanical linkages including releasable links and hooks, frangible links, hooks that may be straightened under tension to slide out of engagement with the staple, a forceps-like grasper, or any other known attachment arrangement.

By resisting the bias of the coil, the first segment 310 and the second segment 320 may be folded together, such folded position being shown in FIGS. 5A-6. This folding together creates potential energy within the coil that, if not resisted, will return the first segment 310 and the second segment 320 to their original, unfolded positions, as shown in FIGS. 4A and 4B. However, when at least the first hook 311 and the second hook 321 of the first segment 310 and the second segment 320, respectively, are inserted into the hollow portion 101 of the tube 100, the walls of the tube 100 provide such resistance, as shown for example in FIG. 6. In this embodiment, at least the first and second hooks 311; 321 are inserted into the hollow interior 101 of the tube portion 100 such that the first and second segments 310; 320 extend from the connection portion 301 such that they are further backward than the connection portion 301. The first segment 310 does not extend as far backward as the second segment 320, as the first segment 310 is not as long as the second segment 320. Thus, a greater amount of forward movement of the rod 200 is required in order to entirely remove the first segment 310 from the tube 100 at the remote end 103, than is required to entirely remove the second segment 320 from the tube 100 at the remote end 103. Thus, the first segment 310 may be returned to its original, non-folded, position independently without returning the second segment 310 to its original, non-folded, position. However, if the amount of this forward movement of the rod 200, which rod is shown in FIGS. 5A and 5B, is great enough, both the first segment 310 and the second segment 320 will have been returned to their original, non-folded, positions.

However, other means for independently removing and thereby exposing the segments 310; 320 may be used, such as using a separate rod for independently moving forward each of the segments, and a malleable connection portion for allowing this independent movement. Additionally, the first segment 310 and second segment 320 may be deployed by alternative means, such as mechanical engagement of the segments 310; 320 of the staple 300 or other fastener (e.g., via one or more pusher rods), natural bias of the material of the fastener, or a separate spring mechanism. Depending on the other means used, segments of the same or different lengths may be employed.

As shown in the steps of FIGS. 1-3, in another aspect of the present invention, there is a method for using a stapler to seal a wound 405 in a stomach of a patient. Although embodiments of the present invention are described in regard to the sealing of a wound 405 in the stomach, those skilled in the art will understand that these devices may be employed in closing openings in the walls of any organ. More specifically, the present invention allows a user to approach an opening in the wall of an organ from within a lumen of that organ and to engage tissue outside the lumen, seal that opening and withdraw the device through the lumen. One of skill in the art will also understand that these devices may have potential utility to close openings, whether intentionally made or accidental, in any tract, canal, cavity or vessel of the body, not just those in organs. Moreover, one of skill in the art will further understand that where embodiments of the invention are described as approaching a wound from the interior 403 of the organ containing that wound, the invention may instead approach the wound 405 from the exterior 404 of the organ containing that wound 405. In this situation, it will be understood that the device will operate on the interior layer 401 of the wall of the organ rather than the exterior layer 402, or the exterior layer 402 rather than the interior layer 401.

First, the remote end 103 of the tube 100 or extending portion is inserted into the interior 403 of the stomach, through an opening into the interior 403 of the stomach. The remote end 103 is then positioned as shown in step 1. This opening may be a natural opening, such as the mouth or the anus, or it may be an artificial opening, such as one created through an incision. An endoscope member may be used to guide this and further movement of the tube. The proximate end 102, the relative location of which is shown in step 3, of the tube 100 or a handle or other attachment attached to the proximate end 102 remains outside of the patient for control of the device.

Then, as shown in step 2, the remote end 103 of the tube 100 is inserted through the wound 405 in the stomach, such that the remote end 103 passes from the interior 403 of the stomach to the exterior 404 of the stomach.

As shown in step 3, the rod 200 is moved forward relative to the tube 100 such that the first segment 310 of the staple 300 extends beyond the remote end 103 of the tube 100. This causes potential energy within the staple 300, such as that stored in the coil, to move the first segment 310 such that it extends approximately perpendicularly to the forward direction of extension of the tube 100, and approximately parallel to the exterior layer 402 of the wall of the stomach, which exterior layer is easier to grasp and safer to puncture than the interior layer 401 of the wall of the stomach. However, the first hook 311 portion of the first segment 310 extends in a different, approximately backwards, direction.

This first hook 311, as shown in steps 4 and 5, is moved by the rod 200 such that it is in contact with a portion 406 of the exterior layer 402 on one side of the wound 405. As shown in step 6, the rod 200 is pulled such that the first hook 311 punctures with its sharp puncturing portion 312, and is pulled approximately backwards into this portion of the exterior layer 402, from which removal is resisted by the first hook's barbed portion 313. Depending on the size of the first hook 311 and the exterior layer 402 of the stomach wall, the first hook 311 may become lodged in the exterior layer 402, an intramuscular/intraserosal stapling in a stomach, or it may travel through the exterior layer and penetrate the interior layer 401, which, in a stomach, is the mucosal/submucosal layer, for a transmural stapling.

Then, as shown in step 7, the rod 200 is moved relative to the tube 100 such that the second segment 320 of the staple 300 extends beyond the remote end 103 of the tube. This causes potential energy within the staple 300, such as that stored in the coil, to move the second segment 320 such that it extends approximately perpendicularly to the forward direction of extension of the tube 100, and approximately parallel to the exterior layer 402 of the stomach. However, the second hook 321 portion of the second segment 320 extends in a different, approximately backwards, direction.

Figure 8:
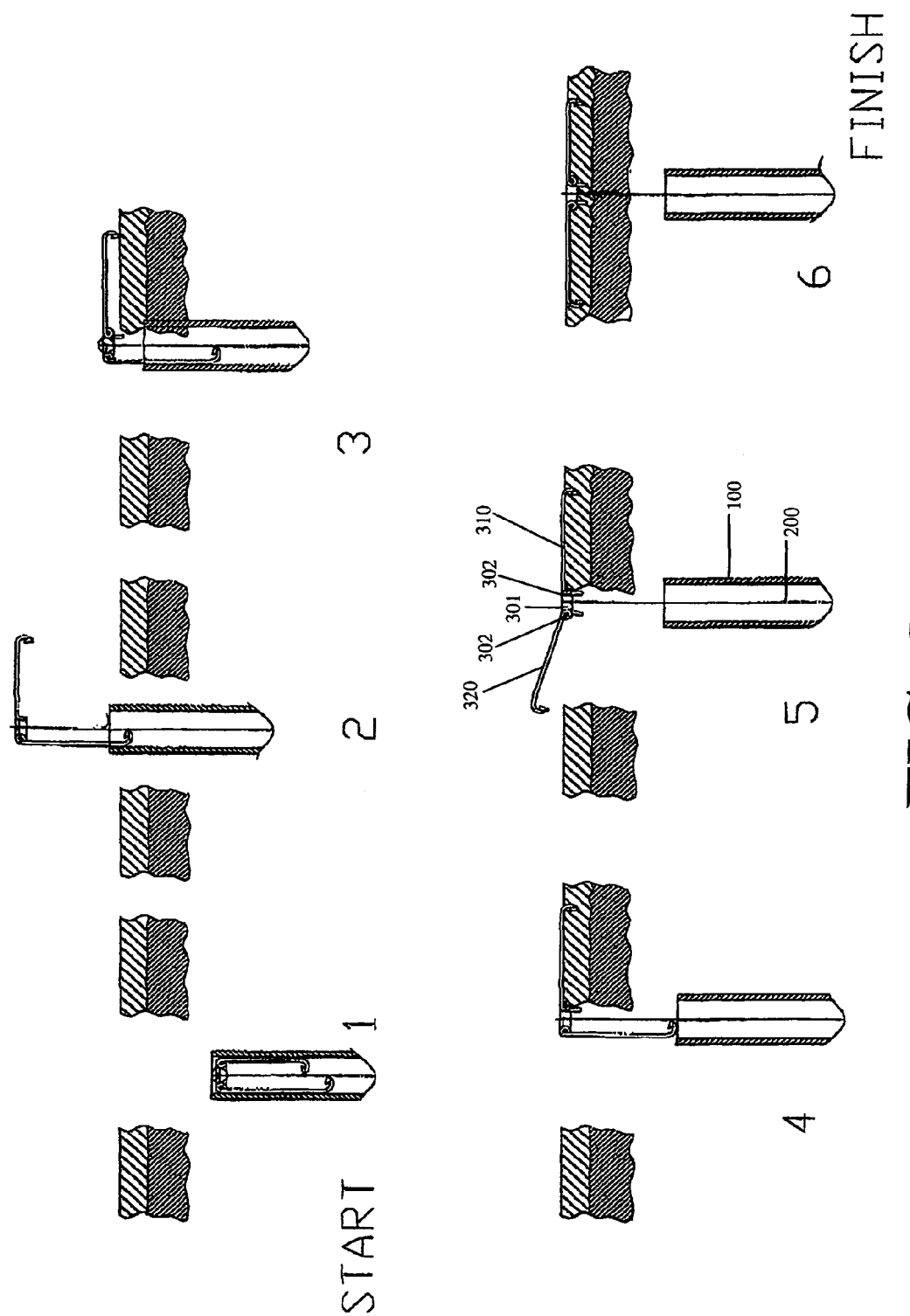
FIG. 8 shows a method of using yet another embodiment of the present invention.

This second hook 321, as shown in steps 7 and 8, is moved by the rod 200 such that it is in contact with a portion 407 of the exterior layer 402 on a second side of the wound 405. This movement may involve, using the first hook 311 as a grasper to move the portion 406 of the tissue on the first side of the wound 405 with the first hook 311 which is embedded in, or has passed through, this portion 406. This movement, as shown in FIG. 8, would result in the portions 406; 407 of the tissue on the two sides of the wound 405 moving closer to each other, and these portions 406; 407 may touch as a result of this pulling, as shown in FIG. 8, facilitating quicker healing.

As shown in step 9, the rod 200 is pulled such that the second hook 321 punctures and is pulled into the portion 407 of the exterior layer 402 on the second side of the wound. Depending on the size of the second hook 321 and the exterior layer 402 of the stomach wall, the second hook 321 may become lodged in the exterior 402 or interior 401 layer, or pass through the wall entirely.

Inserting the staple 300 from the exterior 404 of the stomach into the exterior layer 402 has the advantage of allowing automatic pressing together of the interior layer 401. This occurs by hydrostatic pressure inside of the stomach causing "buckling" of the interior layer 401. Because the staple 300 is not attached in the interior, the portions of the interior layer 401 on opposite sides of the wound 405 are not stopped from pressing together as a result of this "buckling." The staple 300 on the exterior operates as a hinge allowing the portions of the interior layer 401 to swing together and stay in place. This beneficially results in faster healing.

The staple 300, as shown in steps 9 and 10, is then detached from the rod 200, such as by rotating the threading mechanism 201 traveling through the rod 200, directly or through an attachment 202 attached to the threading mechanism 201. However, if another means of attachment of the rod 200 to the staple 300 is used, another method of detachment may therefore be necessary. The rod 200 and tube 100 are then removed from the patient through the opening, such as by pulling on them and feeding them back out of the esophagus and mouth or anus or the artificial opening, the end result of which is shown in step 10.

This method may be used to staple wounds in lumen-containing organs other than the stomach, such as wounds in the large or small intestines. The remote end of the tube is instead inserted into these other lumen-containing organs and through the wound to the exterior of the lumen-containing organs, and the staples are instead used to puncture the walls of these organs from their exterior. Depending, among other considerations, on the particular lumen-containing organ to be operated upon, the opening is chosen accordingly, with the mouth, anus, and vagina being non-limiting examples of such openings.

This method may also be used to staple together other material separated by a gap 405, including material not within a living organism. If the side of the material located closer to the proximate end of the tube, that is, the "near" layer, is directly accessible, then insertion and removal of the tube 100 through an opening will not be necessary. This method advantageously allows for grasping and puncturing of material on the far side 404 of the gap 405 without the need for the tube 100 to approach from the far side 404 of the gap 405.

Figure 7:
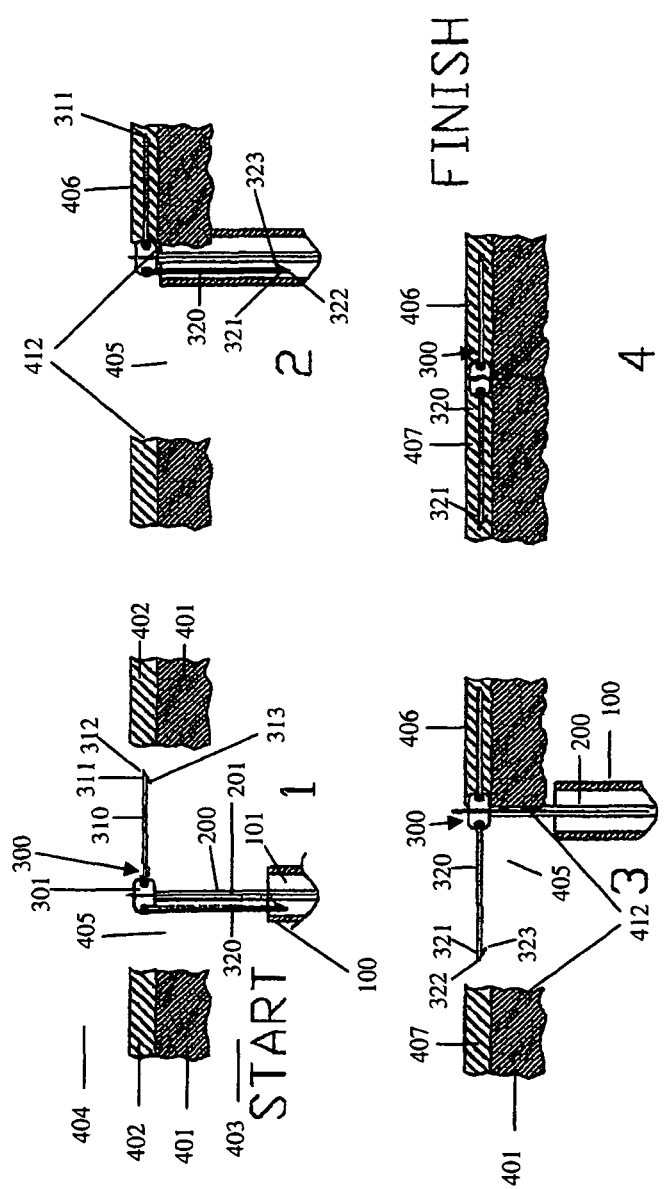
FIG. 7 shows a method of using another embodiment of the present invention.

In yet another aspect of the invention, shown in FIG. 7, there is another method for using a stapler to seal a wound 405 in a stomach of a patient. This method differs from the method described above because the hooks 311; 321 extend in the same direction as the segments 310; 320. Thus, as shown in step 2, in this method the first hook 311 punctures and engages the side-edge 412 of the wound 405 at a portion 406 of the exterior layer 402 at one side of the wound 405. The second segment 320 and second hook 321 are then exposed, as shown in step 3. As shown in step 4, the portion 406 on the one edge of the wound 405 is brought near the portion 407 on a second side of the wound 405, and the second segment 320 and its second hook 321 puncture this latter portion 407. As also shown in steps 3 and 4, detachment of the rod 200 and tube 100 from the staple 300 also occurs, as described above. As the side-edges 412 of walls, rather than the exterior of the walls, are engaged, it is not necessary in this method to insert the tube 100 through the wound to the exterior 404 of the stomach. Avoiding this insertion of the tube 100 has the advantage of decreasing the likelihood of trauma to organs external to the organ being operated upon. Additionally, since the segments 310; 320 need not contain a curved hook, they may have minimal width when folded, and can thus fit within a comparatively small tube.

Inserting the staple 300 into the side-edge 412 of the walls of the stomach has the advantage of allowing automatic pressing together of the portions of the interior layer 401 on opposite sides of the wound 405. This occurs by hydrostatic pressure inside of the stomach causing "buckling" of the interior layer 401. Because the staple 300 is not attached at the interior layer 401, the portions of the interior layer 401 on opposite sides of the wound 405 are not prevented from pressing together as a result of this "buckling." The staple 300 inserted into the side-edges 412 of the stomach wall operates as a hinge allowing the portions of the interior layer 401 to swing together and stay in place. This beneficially results in faster healing.

This method may also be used to staple or fasten together other material separated by a gap 405, including walls of other lumen-containing organs and material not within a living organism. If the side of the material located closer to the proximate end of the tube, that is, the "near" layer corresponding to the proximate layer 401 of the figures, is directly accessible, then insertion and removal of the tube 100 through an opening will not be necessary. This method advantageously allows for grasping and puncturing of material on the sides of the gap 405 without the need that the gap 405 have the full width of the unfolded staple 300.

In yet another embodiment of the invention, the use of which is shown in FIG. 8, hinges 302 in the connection portion 301 are used to attach the two segments to the connection portion 301. At least a portion of the rotation of the segments 310; 320 to the rotational position they occupy during puncturing or impaling may occur by pressing portions of the segments 310; 320 against the tissue. Compared to the device shown in, for example, FIG. 1, when the segments 310; 320 in this yet another embodiment are removed from the tube 100, they open away from the rod 200 in a less forceful manner, as no coil or other holder of stored potential energy is used for this opening. This lowers the chance of injury to the tissue from such force. The hinges 302 and connection portion 301 in this embodiment prevent rotation of the segments 310; 320 about the hinge more than a certain extent, which certain extent is, in one embodiment, ninety degrees, although it may also be more or less in other embodiments. The use of a hinge which limits rotation in this fashion has the advantage of providing for minimal bending or rotation of the segment 310; 320 to occur during puncturing or impaling of the material, which bending or rotation might otherwise result in a less accuracy. However, other appropriate means of connection of the connection portion 301 to the segments 310; 320 may be used in other embodiments, such as a bendable continuation of the segments and/or the connection portion.

Figure 9:
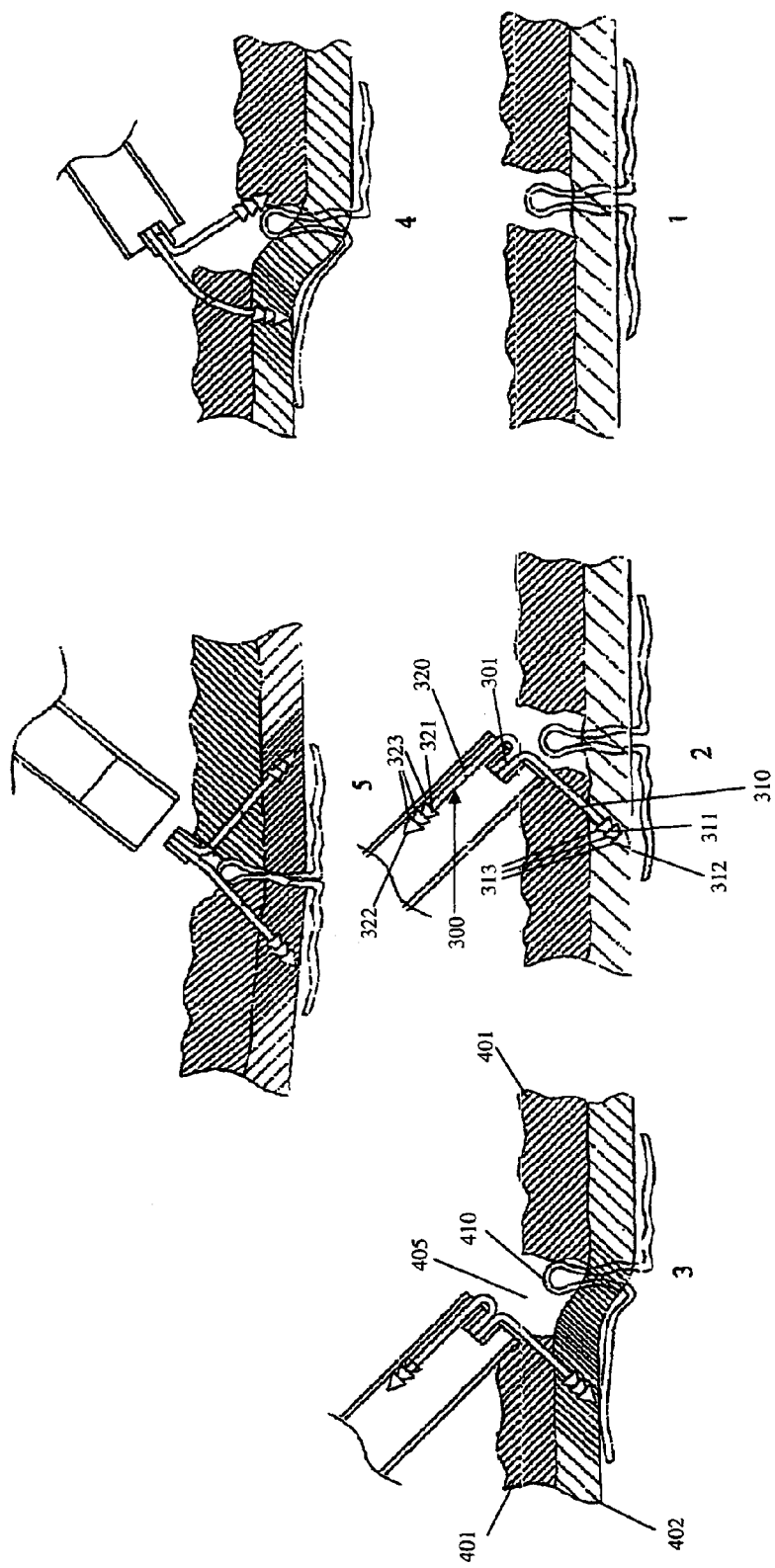
FIG. 9 shows a method of using a further embodiment of the present invention.

In another embodiment of the invention, the use of which is shown in FIG. 9, each hook 311; 321 contains multiple barbed portions 313; 323 at different distances along the hook. This allows for the hooks 311; 321 to become more secure in the tissue than when there is only a single barbed portion, and also allows for force applied by the barbed portions 313; 323 to the tissue to be more diffuse, lessening the chance of tissue damage.

In yet another aspect of the invention, there is a method for "pinching" a bleeding vessel 410 to reduce bleeding, shown in FIG. 9. In this method, the first hook 311 is inserted through the interior layer 401 into the exterior layer 402 on one side of the bleeding vessel 410, and in this process compresses the punctured tissue. These layers are pulled by the first hook 311 in the direction approximately from exterior layer 402 to interior layer 401. The second hook 321 is inserted in a like manner on a second side of the bleeding vessel 410. As the staple 300 is detached from the holding means and the tissue is allowed to return towards its original uncompressed position, the portions of the interior layer 401 on each side of the bleeding vessel 410 move towards each other, "pinching" the bleeding vessel 410.

Figure 12:
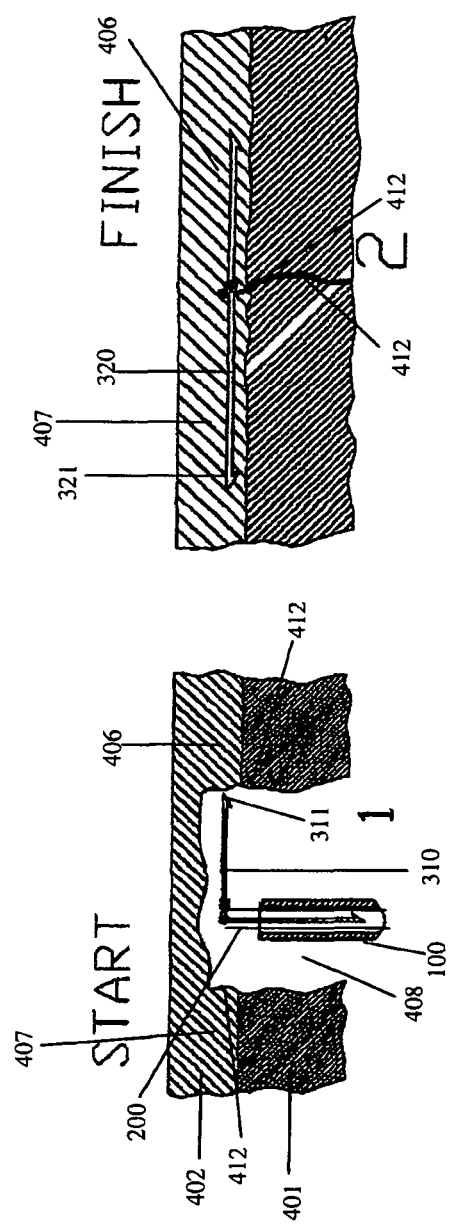
FIG. 12 shows a method of correcting an ulcer-like lesion.

In another aspect of the invention, shown in FIG. 12, there is a method for decreasing the size of an ulcer-like lesion 408 by compressing the portion 406 of the material on one side of the ulcer-like lesion 408 with a first segment 310 which is at least partially inserted into this portion 406 approximately parallel to the layers 401; 402 of the tissue through the side-edge 412 of the ulcer-like lesion 408, compressing the portion 407 of the material on a second side of the ulcer-like lesion 408 with a second segment 320 which is inserted into the portion 407 in a similar fashion, allowing the compressed portions 406; 407 to decompress, and removing the tube 100 and rod 200.

Figure 10:
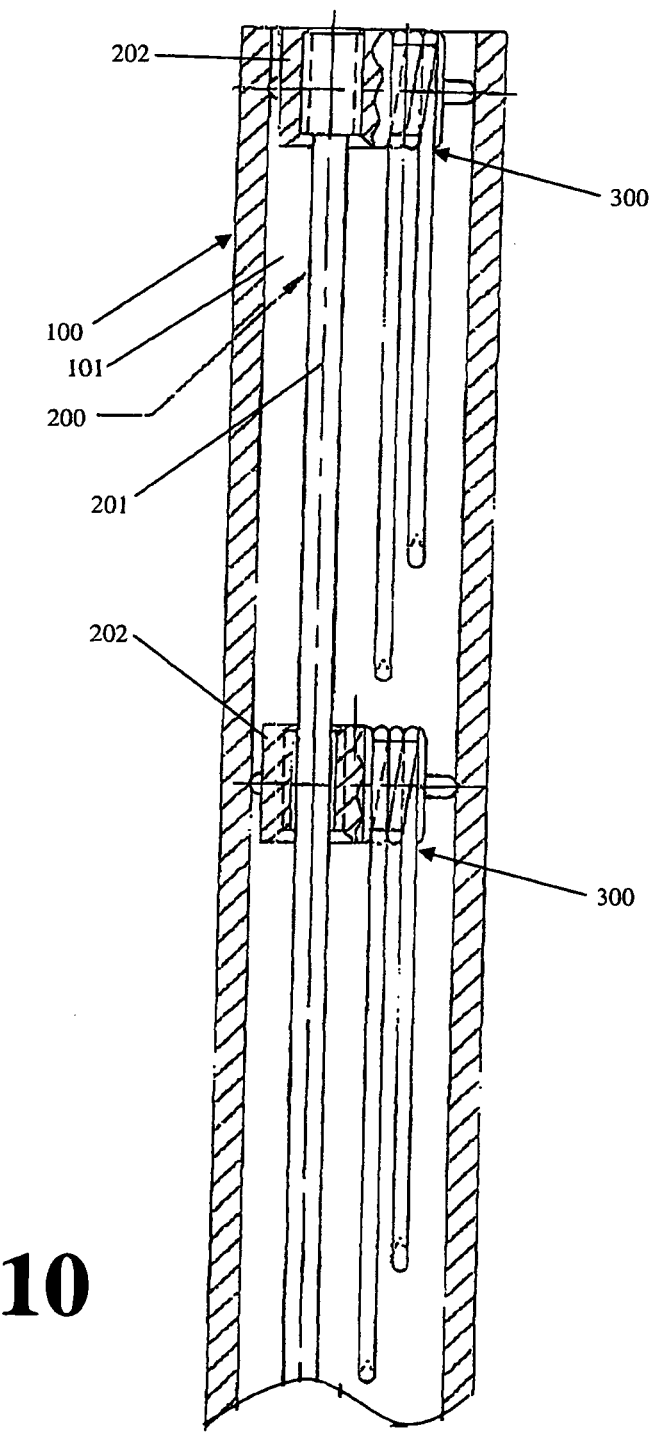
FIG. 10 is a side-view of the remote portion of the device according to an embodiment of the device which holds more than one staple.

In yet another embodiment of the invention, shown in FIG. 10, multiple staples 300 or fasteners are stored within the tube 100. Each is detachably connected to the rod 200 disclosed within the tube 100 by an attachment mechanism 202. This allows for multiple staples 300 to be used without the need to take time during an operation to reload staples or to remove the tube 100 from the patient. The staples 300 may be detached, through the rotation of the threading mechanism 201 as discussed previously in this specification.

Figure 11A:
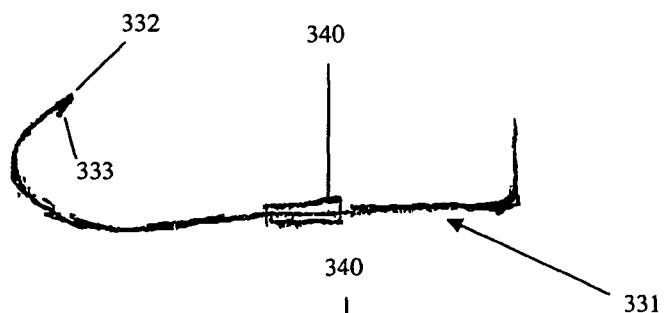
FIG. 11A is a side-view of a hook of a staple according to yet another embodiment of the present invention having multiple branching subsections.
Figure 11B:
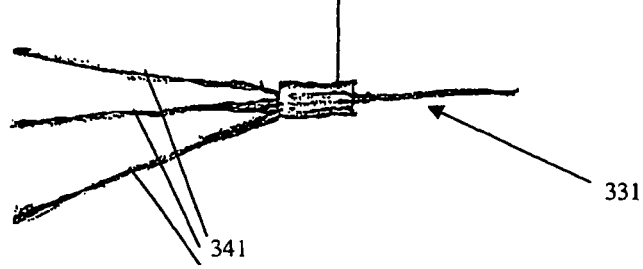
FIG. 11B is a top-view of this hook.
Figure 11C:
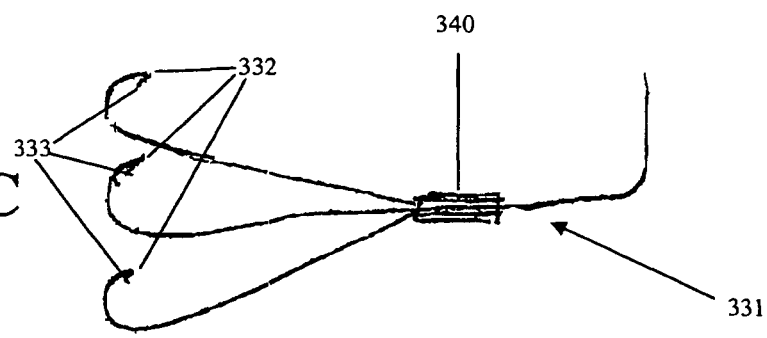
FIG. 11C is a view of this hook from a position above and to the side of this hook.

In another embodiment of the invention, shown in FIGS. 11A-11C, a hook 331 with multiple subsections 341 may be used in the device, each of which subsections 341 has a sharp puncturing portion 332 and a barbed portion 333. The multiple subsections are secured by a sheathe 340 connecting the subsections to the rest of the hook 331 and/or maintaining the appropriate displacement between the multiple subsections 341. This embodiment advantageously allows for a strong connection between the hook 331 and the tissue, and the securing of a larger amount of tissue. Additionally, as there are multiple puncturing portions 332 on each hook 331, force used to move the material on one side of the gap/wound towards material on a second side of the gap/wound is dispersed over multiple points in the material, decreasing the likelihood of trauma from this movement.

The preceding description is presented to enable one of ordinary skill in the art to make and use the invention and to incorporate it in the context of particular applications. Various modifications, such as the use of various non-staple fasteners, as well as a variety of uses in different applications will be readily apparent to those skilled in the art, and the general principles defined herein may be applied to a wide range of embodiments. Thus, the present invention is not intended to be limited to the embodiments presented, but is to be accorded the widest scope consistent with the principles and novel features disclosed herein.

What is claimed is:

1. A material-joining device comprising:
a first fastener having first and second segments, the first and second segments being coupled to one another via a spring coupled between first ends of the first and second segments, the first and second segments extending away from the spring to respective tissue piercing free ends; and
a housing which holds the first fastener in an insertion configuration with the free ends of the first and second segments positioned proximally of the spring, the first fastener being movable relative to the housing from the insertion configuration to an initial deployment configuration in which only the first segment extends distally from the housing so that the free end of the first segment may be inserted into a first portion of tissue, the first fastener being movable relative to the housing from the initial deployment configuration to a second deployment configuration in which the second segment extends distally from the housing so that the free end of the second segment may be inserted into a second portion of tissue.

2. The device of claim 1, further comprising:
an exposing mechanism configured to expose the first segment independently of exposing the second segment, and configured to expose the second segment.

3. The device of claim 2, wherein a part of the first fastener stores potential energy and applies the stored potential energy to the first and second segments, the exposing mechanism countering the potential energy to maintain the first fastener in the insertion configuration.

4. The device of claim 1, wherein the first segment is a first hook, and the second segment is a second hook.

5. The device of claim 4, wherein at least one of the first hook and the second hook comprises at least one sharp puncturing portion and at least two barbed portions.

6. The device of claim 1, wherein at least one of the first segment and the second segment comprises at least two subsections, each of which subsections has a sub-mechanism configured to secure the first and second portions of tissue, respectively.

7. The device of claim 6, wherein the sub-mechanism comprises a sharp puncturing portion and a barbed portion.

8. The device of claim 1, further comprising a second fastener, wherein the housing holds the first and second fasteners simultaneously.

9. The device of claim 1, wherein the housing extends along a first axis in one direction from the first fastener, and wherein the first segment and the second segment are positioned such that, when securing the first and second portions of tissue, they each extend at an angle relative to the first axis.

10. The device of claim 9, wherein the first segment and the second segment are positioned such that, when securing the first and second portions of tissue, they extend in approximately opposite directions from each other.

11. The device of claim 1, wherein the first segment includes a proximal portion and a distal portion angled with respect to the proximal portion with the spring biased so that, when the first fastener is extended from the housing to the initial deployed configuration, the proximal portion extends radially away from the housing while the free end faces proximally.

12. The device of claim 1, wherein the first and second segments are integrally formed from a length of wire and the spring is formed as a coil in the wire.

13. The device of claim 1, wherein when in the second deployment configuration, the first and second segments are biased by the spring toward a position in which proximal portions of the first and second segments extend away from a longitudinal axis substantially parallel to one another in opposite directions.

14. A material-joining device comprising:
a first fastener having first and second segments extending from a connection portion at a first end to respective free ends, wherein the first segment secures tissue independently of the second segment;
a holding mechanism releasably holding the connection portion of the first fastener with free ends of the first fastener positioned proximally of the connection portion; and
an exposing mechanism configured to expose the first segment independently of exposing the second segment, and configured to expose the second segment, wherein the exposing mechanism comprises a part of the first fastener storing potential energy and applying the stored potential energy to the first and second segments and a resisting mechanism countering the potential energy to maintain the first fastener in a first insertion configuration, wherein the part of the first fastener storing potential energy is a coil.

15. The device of claim 14, wherein the second segment has a longer length than the first segment, wherein the resisting mechanism is a tubular member having a proximate end and a remote end, the first fastener being housed within the tubular member in the first insertion configuration, the first fastener being movable to a second partially deployed configuration in which the entire first segment extends distally of the remote end of the tubular member and the second segment is housed within the tubular member.

16. A stapler comprising:
a tubular member extending from a proximate end to a remote end along a first axis;
a rod at least partially disposed within the tubular member and extending along an axis aligned with the first axis; and
a staple having first and second segments, the first and second segments being coupled to one another via a spring coupled between first ends of the first and second segments, the first and second segments extending away from the spring to respective tissue piercing free ends, the staple being removably attached to the rod and housed within the tubular member in a first insertion configuration in which the free ends of the first and second segments are positioned proximally of the spring, the staple being movable to an initial deployment configuration in which only the first segment extends distally from the tubular member so that the free end of the first segment may be inserted into a first portion of tissue, the staple being movable relative to the tubular member from the initial deployment configuration to a second deployment configuration in which the second segment extends distally from the housing so that the free end of the second segment may be inserted into a second portion of tissue.

17. The device of claim 16, wherein the staple is configured such that potential energy stored in the staple when it is folded in the first insertion configuration is directed to move the staple to the initial deployment configuration as the first segment is extended out of the tubular member.

18. The device of claim 17, wherein the staple is further configured such that the potential energy causes the first segment to extend substantially perpendicularly to the first axis when the staple is moved distally along the first axis by the rod relative to the tubular member to assume the second deployment configuration.

19. The device of claim 18, wherein in the second deployment configuration, the entire second segment is extended distally beyond the remote end of the tubular member, the potential energy extending the second segment substantially perpendicularly to the first axis in a direction substantially opposite a direction of extension of the first segment.

20. The device of claim 19, wherein the staple is further configured such that when the first and second segments are moved to the second deployment configuration, first and second hooks positioned at the free ends of the first and second segments are in a proximal-facing orientation to permit capture of tissue proximal of the spring.

* * * * *